US010821441B2

(12) United States Patent
Vanapalli et al.

(10) Patent No.: US 10,821,441 B2
(45) Date of Patent: Nov. 3, 2020

(54) MICROFLUIDIC DEVICES AND METHODS FOR BIOASSAYS

(71) Applicant: Texas Tech University System, Lubbock, TX (US)

(72) Inventors: Siva A. Vanapalli, Lubbock, TX (US); Swastika S. Bithi, Lubbock, TX (US)

(73) Assignee: Texas Tech Univeristy System, Lubbock, TX (US)

( * ) Notice: Subject to any disclaimer, the term of this patent is extended or adjusted under 35 U.S.C. 154(b) by 0 days.

(21) Appl. No.: 15/580,439

(22) PCT Filed: Jun. 10, 2016

(86) PCT No.: PCT/US2016/036787
§ 371 (c)(1),
(2) Date: Dec. 7, 2017

(87) PCT Pub. No.: WO2016/201163
PCT Pub. Date: Dec. 15, 2016

(65) Prior Publication Data

US 2018/0185847 A1 Jul. 5, 2018

Related U.S. Application Data

(60) Provisional application No. 62/173,477, filed on Jun. 10, 2015.

(51) Int. Cl.
*B01L 3/00* (2006.01)
*G01N 33/00* (2006.01)

(52) U.S. Cl.
CPC ... *B01L 3/502784* (2013.01); *B01L 3/502715* (2013.01); *B01L 3/502746* (2013.01);
(Continued)

(58) Field of Classification Search
CPC ........ C12M 47/02; C12M 47/00; G01N 33/00
(Continued)

(56) References Cited

U.S. PATENT DOCUMENTS

2003/0138359 A1 7/2003 Chow et al.
2009/0266421 A1 10/2009 Linder et al.
(Continued)

FOREIGN PATENT DOCUMENTS

WO 2009139898 A2 11/2009

OTHER PUBLICATIONS

Boukella, H et al, Simple, robust storage of drops and fluids in a microfluidic device†, Lab Chip, 2009, 9, 331-338. (Year: 2009).*
(Continued)

*Primary Examiner* — Christine T Mui
(74) *Attorney, Agent, or Firm* — Daniel J. Chalker; Edwin S. Flores; Chalker Flores, LLP

(57) ABSTRACT

A microfluidic device includes a substrate and a cover. The substrate has an inlet port, a first microchannel, one or more parking loops, a second microchannel and an outlet port for each microchannel network. The first microchannel is connected to the inlet port, the second microchannel is connected to the outlet port, the parking loops are connected between the first and second microchannels. Each parking loop includes a parking loop inlet, a parking loop output, a fluidic trap connected between the parking loop inlet and the parking loop outlet, and a bypass microchannel connected to the parking loop inlet and the parking loop outlet. The cover is attached to a top of the substrate and has an inlet opening and an outlet opening through the cover for each microchannel network. The inlet and outlet openings of the cover are disposed above the inlet and outlet ports in the substrate.

20 Claims, 9 Drawing Sheets

(52) U.S. Cl.
CPC ... *B01L 3/502761* (2013.01); *B01L 3/502707* (2013.01); *B01L 2200/12* (2013.01); *B01L 2200/142* (2013.01); *B01L 2300/041* (2013.01); *B01L 2300/087* (2013.01); *B01L 2300/088* (2013.01); *B01L 2300/0816* (2013.01); *B01L 2300/0887* (2013.01); *B01L 2400/049* (2013.01); *B01L 2400/084* (2013.01)

(58) Field of Classification Search
USPC ................................................ 436/63; 435/2
See application file for complete search history.

(56) References Cited

U.S. PATENT DOCUMENTS

| | | | |
|---|---|---|---|
| 2010/0163109 | A1 | 7/2010 | Fraden et al. |
| 2010/0252118 | A1 | 10/2010 | Fraden et al. |
| 2014/0051062 | A1 | 2/2014 | Vanapalli et al. |

OTHER PUBLICATIONS

Bithi, Coalescing drops in microfluidic parking networks: A multifunctional platform for drop-based microfluidics, Biomicrofluidics 8, 034118 (2014). (Year: 2014).*
Bithi, Supporting Information, Coalescing drops in microfluidic parking networks: A multifunctional platform for drop-based microfluidics, Biomicrofluidics 8, 034118 (2014) (Year: 2014).*
International Search Report (KIPO) PCT/US2012/036815 dated Nov. 14, 2012.
Huebner, A. et al., Microdroplets: A sea of applications? Lab on a Chip 8 (8), 1244-1254 (2008).
Song, H. et al., Reactions in droplets in microfluidic channels. Angewwandte Chemie—International Edition 45 (44), 7336-7356 (2006).
Teh, S. Y. et al., Droplet microfluidics. Lab on a Chip 8 (2), 198-220 (2008).
Zheng, B. et al., Screening of protein crystallization conditions on a microfluidic chip using nanoliter-size droplets. Journal of the American Chemical Society 125 (37), 11170-11171 (2003).
Shim, J. U. et al., Using microfluidics to decouple nucleation and growth of protein crystals. Crystal Growth & Design 7(11), 2192-2194 (2007).
Zhang, Y. H. et al., Microfluidic DNA amplification—A review. Analytica Chimica Acta 638 (2), 115-125 (2009).
Shen, F. et al., Nanoliter Multiplex PCR Arrays on a SlipChip. Analytical Chemistry 82 (11), 4606-4612 (2010).
Beer, N. R. et al, On-chip, real-time, single-copy polymerase chain reaction in picoliter droplets. Analytical Chemistry 79 (22), 8471-8475 (2007).
Mohr, S. et al., Numerical and experimental study of a droplet-based PCR chip. Microfluidics and Nanofluidics 3 (5), 611-621 (2007).
Wang, F. et al., Performance of nanoliter-sized droplet-based microfluidic PCR. Biomedical Microdevices 11 (5), 1071-1080 (2009).
Agresti, J. J. et al., Ultrahigh-throughput screening in drop-based microfluidics for directed evolution (vol. 170, p. 4004, 2010). Proceedings of the National Academy of Sciences of the United States of America 107 (14), 6550-6550 (2010).
Koster, S. et al., Drop-based microfluidic devices for encapsulation of single cells. Lab on a Chip 8 (7), 1110-1115 (2008).
He, M. Y. et al., Selective encapsulation of single cells and subcellular organelles into picoliter- and femtoliter-volume droplets. Analytical Chemistry 77 (6), 1539-1544 (2005).
Kumaresan, P. et al., High-Throughput Single Copy DNA Amplification and Cell Analysis in Engineered Nanoliter Droplets. Analytical Chemistry 80 (10), 3522-3529 (2008).
Brouzes, E. et al., Droplet microfluidic technology for single-cell high-throughput screening. Proceedings of the National Academy of Sciences of the United States of America 106 (34), 14195-14200 (2009).
Kobel, S. et al., Optimization of microfluidic single cell trapping for long-term on-chip culture. Lab on a Chip 10 (7), 857-863 (2010).
Baret, J. C. et al, Quantitative Cell-Based Reporter Gene Assays Using Droplet-Based Microfluidics. Chem. Biol. 17(5), 528-536 (2010).
Marcoux, P. R. et al., Micro-confinement of bacteria into w/o emulsion droplets for rapid detection and enumeration. Colloid Surf. A—Physicochem. Eng. Asp. 377 (1-3), 54-62 (2011).
Park, J. et al., Microdroplet-Enabled Highly Parallel Co-Cultivation of Microbial Communities. PLoS ONE 6 (2), e17019 (2011).
Dendukuri, D. et al., Controlled synthesis of nonspherical microparticles using microfluidics. Langmuir 21 (6), 2113-2116 (2005).
Dendukuri, D. et al., The synthesis and assembly of polymeric microparticles using microfluidics. Advanced Materials 21, 1-16 (2009).
Shestopalov, I. et al., Multi-step synthesis of nanoparticles performed on millisecond time scale in a microfluidic droplet-based system. Lab on a Chip 4 (4), 316-321 (2004).
Shah, R. K. et al., Designer emulsions using microfluidics. Materials Today 11, 18-27 (2008).
Thorsen, T. et al., Dynamic pattern formation in a vesicle-generating microfluidic device. Physical Review Letters 86(18), 4163-4166 (2001).
Bithi, S. S. et al., Behavior of a train of droplets in a fluidic network with hydrodynamic traps. Biomicrofluidics 4 (4), 10 (2010).
Xia, Y. N. et al., Soft lithography. Annual Review of Materials Science 28, 153-184 (1998).
Sun, M. et al., Microfluidic static droplet arrays with tuneable gradients in material composition. Lab Chip 11, 3949-3952 (2011).
Nie, Z. et al., Janus and ternary particles generated by microfluidic synthesis: Design, synthesis and self-assembly. Journal of American Chemical Society 128, 9408-9412 (2006).
Christopher, G. F. et al., Microfluidic methods for generating continuous droplet streams. J Phys D Appl Phys 40(19), R319-R336 (2007).
Anna, S. L. et al., Formation of dispersions using "flow focusing" in microchannels. Applied Physics Letters 82 (3), 364-366 (2003).
Tan, W. H. et al., Monodisperse alginate hydrogel microbeads for cell encapsulation. Advanced Materials 19 (18), 2696-+ (2007).
Um, E., et al., Random breakup of microdroplets for single-cell encapsulation. Applied Physics Letters 97 (15) (2010).
International Search Report [PCT/US2016/036787] (KR/RO) dated Sep. 26, 2016.

* cited by examiner

MICROFLUIDIC DEVICES AND METHODS FOR BIOASSAYS

CROSS-REFERENCE TO RELATED APPLICATIONS

This application is the National Stage of International Application No. PCT/US2016/036787, filed on Jun. 10, 2016, which claims priority to U.S. Provisional Patent Application Ser. No. 62/173,477, filed on Jun. 10, 2015. The contents of both applications are incorporated by reference herein in their entirety.

STATEMENT OF FEDERALLY FUNDED RESEARCH

This invention was made with U.S. Government support awarded by NSF grant numbers 1150836, 1355920 and 1445070. The government has certain rights in this invention.

FIELD OF THE INVENTION

The present invention relates generally to the field of microfluidics, and more particularly to microfluidic devices for bioassays.

BACKGROUND OF THE INVENTION

There is a growing interest in conducting drug screens with primary cells derived from human tissues and biofluids to predict patient outcomes. In contrast to immortalized cell lines, primary cells are a scarce resource and yet preclinical studies demand diverse assays probing specific targets, off-targets and cytotoxicity. Therefore there is a need for a technology that can to screen drugs with minimal requirements on cell sample and compound volumes. Currently, multiwell plates and pipetting systems are the established methods for drug assays. However, this technology is difficult to scale down to nanoliter volumes due to fluid evaporation and pipetting errors. In recent years, drop-based microfluidics has emerged as a powerful technology to compartmentalize cells in volumes down to picoliters. Despite its great potential, drop-based microfluidics has not been configured to conduct cell based drug assays with the same ease and parallelized fluid handling capability as well plates and pipetting systems.

SUMMARY OF THE INVENTION

One embodiment of the present invention provides a microfluidic device having one or more microchannel networks. The microfluidic device includes a substrate and a cover. The substrate has an inlet port, a first microchannel, one or more parking loops, a second microchannel and an outlet port for each microchannel network. The first microchannel is connected to the inlet port, the second microchannel is connected to the outlet port, the one or more parking loops are connected between the first microchannel and the second microchannel. Each parking loop includes a parking loop inlet, a parking loop output, a fluidic trap connected between the parking loop inlet and the parking loop outlet, and a bypass microchannel connected to the parking loop inlet and the parking loop outlet. The cover is attached to a top of the substrate and has an inlet opening and an outlet opening through the cover for each microchannel network. The inlet opening of the cover is disposed above the inlet port in the substrate and the outlet opening is disposed above the outlet port in the substrate.

Another embodiment of the present invention provides a method of making a microfluidic device having one or more microchannel networks. An inlet port, a first microchannel, one or more parking loops, a second microchannel and an outlet port are formed in a substrate for each microchannel network. The first microchannel is connected to the inlet port, the second microchannel is connected to the outlet port, the one or more parking loops are connected between the first microchannel and the second microchannel. Each parking loop includes a parking loop inlet, a parking loop output, a fluidic trap connected between the parking loop inlet and the parking loop outlet, and a bypass microchannel connected to the parking loop inlet and the parking loop outlet. An inlet opening and an outlet opening through a cover layer are formed for each microchannel network. The cover is attached to a top of the substrate. The inlet opening of the cover is disposed above the inlet port in the substrate and the outlet opening is disposed above the outlet port in the substrate for each microchannel network.

Yet another embodiment of the present invention provides a method for trapping a sample within a microfluidic device having one or more microchannel networks. A microfluidic device is provided. The microfluidic device includes a substrate having an inlet port, a first microchannel, one or more parking loops, a second microchannel and an outlet port for each microchannel network. The first microchannel is connected to the inlet port, the second microchannel is connected to the outlet port, the one or more parking loops are connected between the first microchannel and the second microchannel. Each parking loop includes a parking loop inlet, a parking loop output, a fluidic trap connected between the parking loop inlet and the parking loop outlet, and a bypass microchannel connected to the parking loop inlet and the parking loop outlet. The microfluidic device also includes a cover attached to a top of the substrate that has an inlet opening and an outlet opening through the cover for each microchannel network. The inlet opening of the cover is disposed above the inlet port in the substrate and the outlet opening is disposed above the outlet port in the substrate. A first oil is released into the inlet port of the substrate via the inlet opening using a pipette. The sample is released into the inlet port of the substrate via the inlet opening using the pipette. Each fluidic trap is filled with the substance by creating a suction in the outlet port of the substrate via the outlet opening using the pipette. A second oil is released into the inlet port of the substrate via the inlet opening using the pipette. The sample is removed from the microchannel network, except for each fluidic trap, by creating a suction in the outlet port of the substrate via the outlet opening using the pipette.

The present invention is described in detail below with reference to the accompanying drawings.

DESCRIPTION OF THE DRAWINGS

The above and further advantages of the invention may be better understood by referring to the following description in conjunction with the accompanying drawings, in which.

DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

Figure 1A:
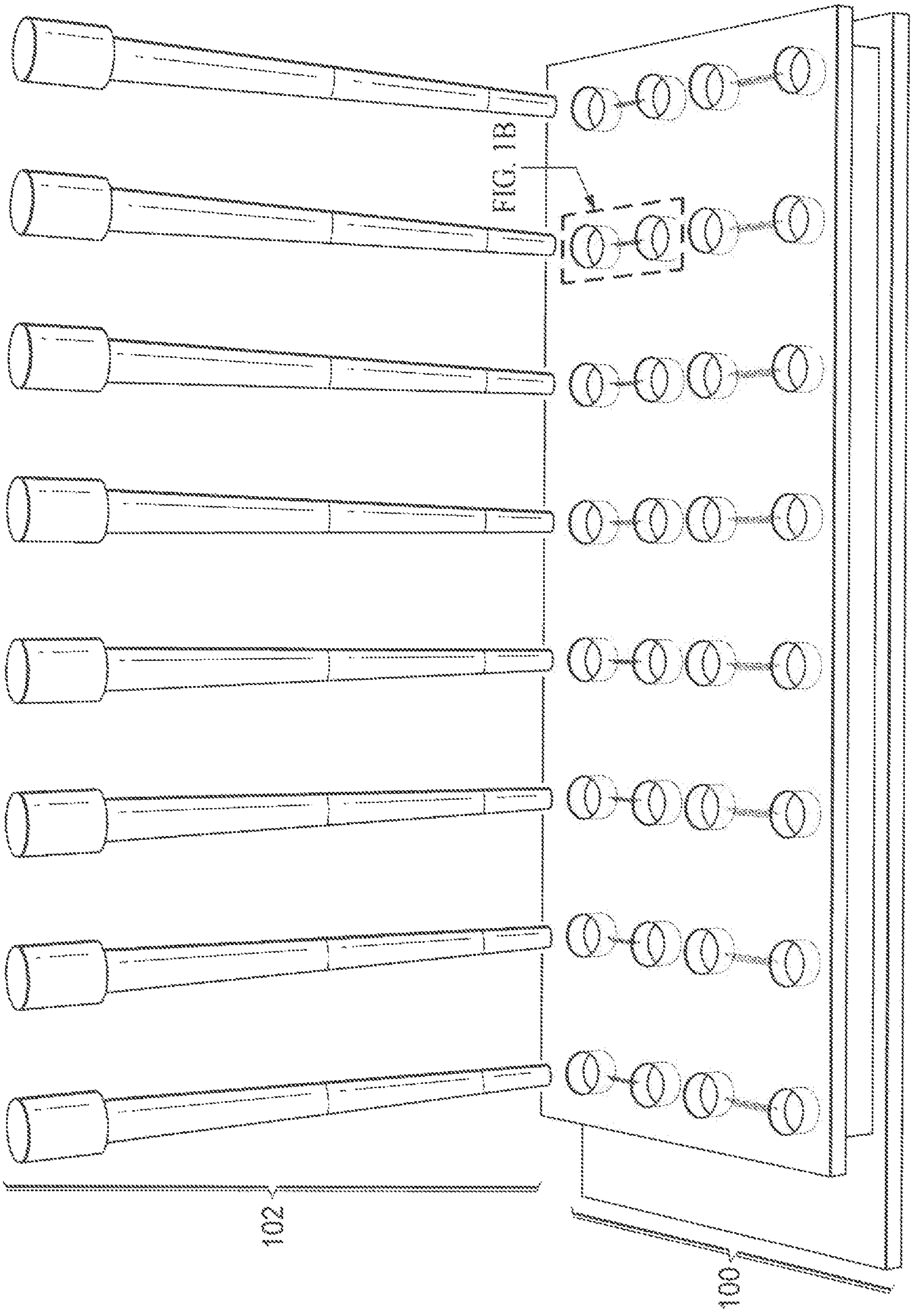
FIG. 1A is an image of a microfluidic device in accordance with one embodiment of the present invention.
Figure 1B:
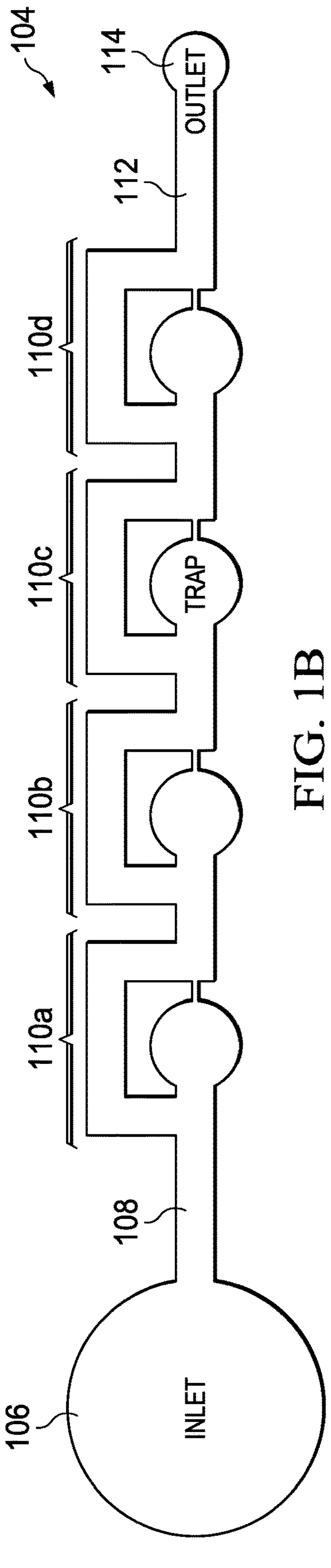
FIG. 1B is a schematic of a single microchannel network within the microfluidic device in accordance with one embodiment of the present invention.

Various embodiments of the present invention provide a microfluidic device for storing arrays of nanoliter droplets. Although the microfluidic device 100 described herein is well suited for use with automated multichannel pipettes 102 as shown in FIG. 1A, the present invention is not limited to use with automated systems. The microfluidic device 100 may include one or more microchannel networks 104 embedded or formed on a substrate. In this example and as shown in FIG. 1B, the microfluidic device 100 contains a set or array of isolated microchannels networks 104 arranged in a grid format. The non-limiting microfluidic device 100 shown in FIG. 1A contains 16 microchannel networks 104 arranged in a 2×8 format. This format allows facile interfacing of an 8-channel pipette. This design can be scaled up to a 12×8 format or larger with the total footprint commensurate with a standard multiwell plate.

Figure 10:
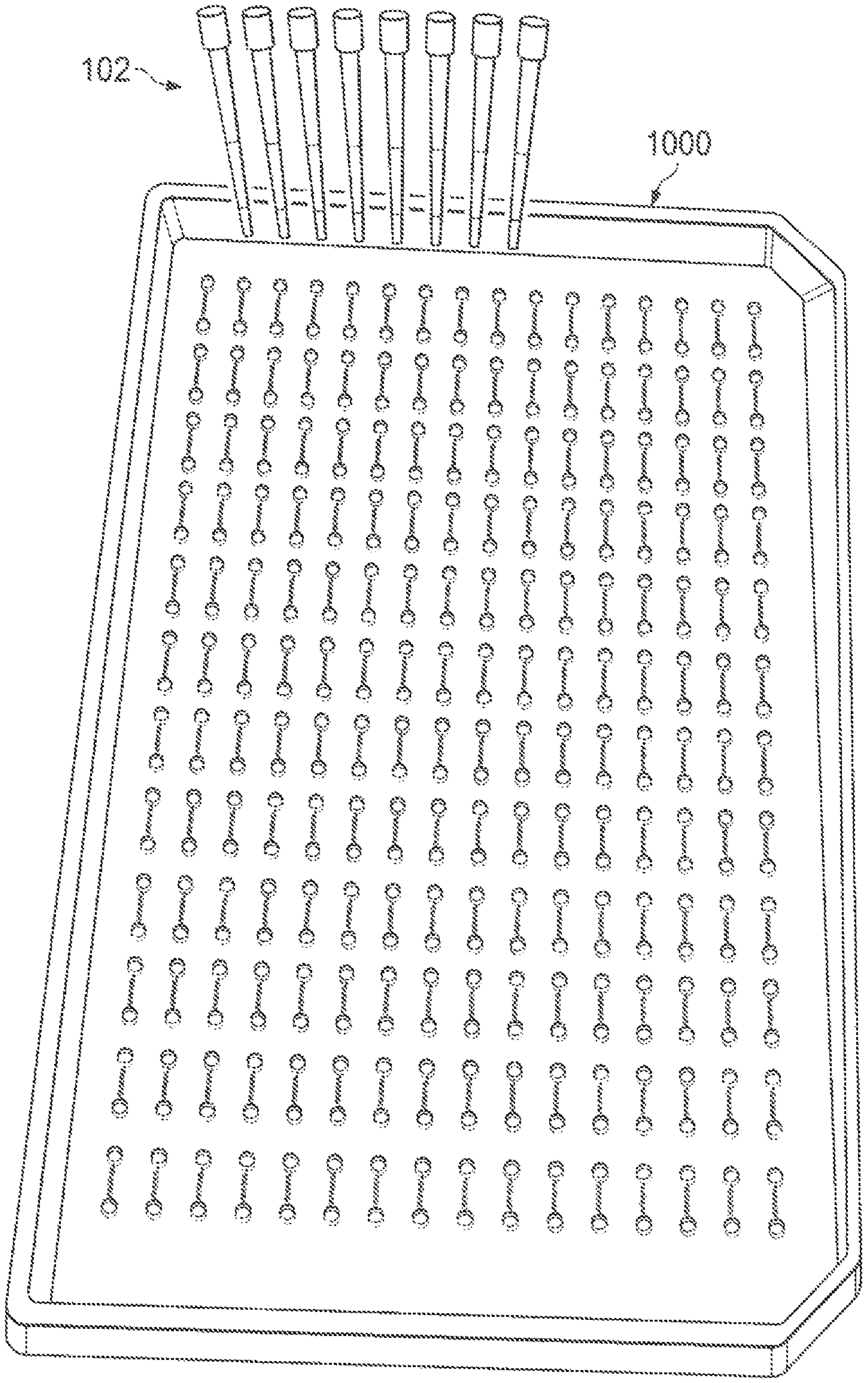
FIG. 10 is an image of a high throughput multiwell plate with an industry standard multichannel pipettor in accordance with one embodiment of the present invention.

For example, FIG. 10 is an image of a high throughput multiwell plate 1000 with an industry standard multichannel pipettor 102. The high throughput multiwell plate 1000 has 192 microchannel networks 104 arranged in a 12×16 format on a footprint equivalent to a standard wellplate that integrates with an 8-channel pipette 102. Other configurations and array sizes can be used.

Figure 1C:
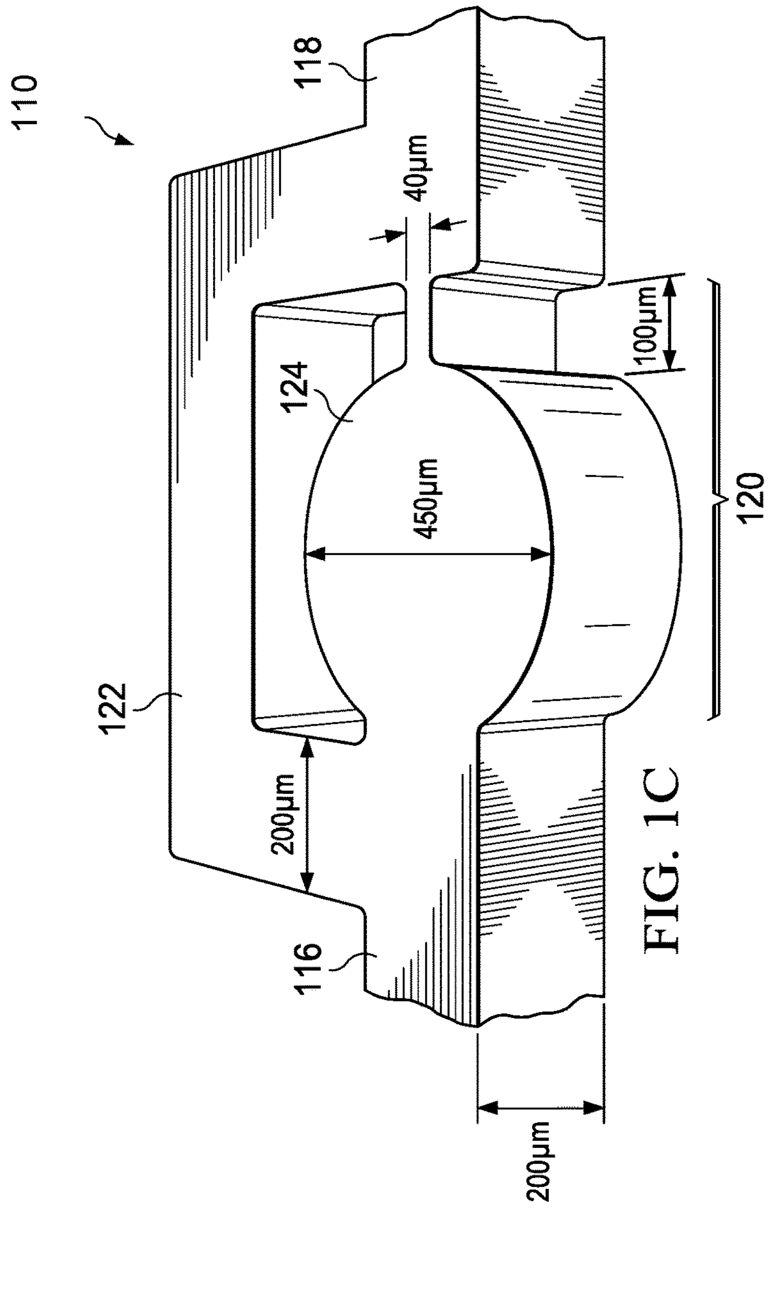
FIG. 1C is a 3D view of a single parking loop containing a fluidic trap to store a sample in accordance with one embodiment of the present invention.

Each embedded microchannel network 104 contains an inlet port or reservoir 106, a first microchannel 108, one or more parking loops 110 (e.g., four parking loops 110*a*, 110*b*, 110*c* and 110*d*), a second microchannel 112 and an outlet port 114. The first microchannel 108 is connected to the inlet port 106 and the second microchannel 112 is connected to the outlet port 114. The one or more parking loops 110 are connected between the first microchannel 108 and the second microchannel 112. As shown in FIG. 1C, each parking loop 110 includes a parking loop inlet 116, a parking loop output 118, a fluidic trap 120 (lower branch) connected between the parking loop inlet 116 and the parking loop outlet 118, and a bypass microchannel 122 (upper branch) connected to the parking loop inlet 116 and the parking loop outlet 118. The fluidic trap 120 includes a trap repository 124 connected to the parking loop inlet 116 and a trap microchannel 126 connecting the trap repository 124 to the parking loop outlet 118. The cross-sectional area of the trap microchannel 126 is smaller than the cross-sectional area of the bypass microchannel 122, which causes the hydrodynamic resistance of the bypass microchannel 122 to be smaller than the hydrodynamic resistance of the fluidic trap 120.

The hydrodynamic resistance ratio between the fluidic trap 120 and bypass microchannel 122 is typically from 1.0 to 2.0, and may be between 1.4 to 1.6 in order to trap and store replicates of nanoliter-scale fluid volumes. In the example, each parking loop 110 has the following dimensions: the first microchannel 108, the second microchannel 112 and the bypass microchannel 122 have a width of approximately 200 μm and a height of approximately 200 μm; the trap repository 124 has a diameter of approximately 450 μm; the trap microchannel 126 has a width of approximately 40 μm; the first microchannel 108, the second microchannel 112, the bypass microchannel 122, the trap repository 124 and the trap microchannel 126 have a height of approximately 200 μm; and the trap microchannel 126 has a length of approximately 100 μm. Each fluidic trap 124 has a volume of only 30 nL in contrast to the 1-10 μL that is currently used in standard multiwell plate. Other dimensions and volumes can be used. For example, volume of the trap repository 124 can be approximately 10, 20, 30, 40, 50, 60, 70, 80, 90 nL or any increment thereof.

Figure 1D:
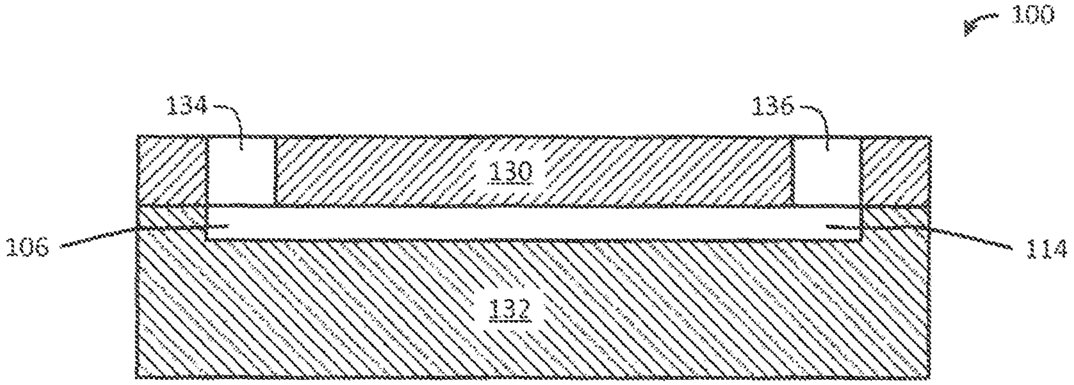
FIG. 1D is a cross-sectional view (not to scale) of a portion of the microfluidic device in accordance with one embodiment of the present invention.

As will be explained in more detail below and as shown in FIG. 1D, the microfluidic device 100 also includes a cover or upper layer 130 attached to a top of the substrate or lower layer 132, which reduces evaporation and increases the viability of samples trapped within the microchannel networks 104. Note that the cross-sectional diagram of a portion of the microfluidic device 100 shown in FIG. 1D is not to scale. The cover 130 can be attached, affixed or integrated to the top of the substrate 132 by any suitable method for the materials in which the substrate 132 and cover 130 are made. For example, the cover 130 can be plasma bonded to the substrate 132 when both the cover 130 and substrate 132 are made of polydimethylsiloxane (PDMS). The cover 130 has an inlet opening 134 and an outlet opening 136 through the cover 130 for each microchannel network 104. Depending on the size of the inlet port 106 and outlet port 114, the cross-sectional area of the inlet opening 134 and outlet opening 136 can greater than, equal to or less than the cross-sectional area of the inlet port 106 and outlet port 114 in the substrate 132. The inlet opening 134 of the cover 130 is disposed above the inlet port 106 in the substrate 132 and the outlet opening 136 is disposed above the outlet port 114 in the substrate 132. Typically the openings 134 and 136 are aligned with the ports 106 and 114. In one non-limiting example, the inlet opening 134 and the outlet opening 136 of the cover 130 have a diameter of approximately 3 mm, and the cover 130 has a thickness of 1 mm.

More information about other embodiments are described in U.S. patent application Ser. No. 14/114,304 filed on May 7, 2012 and entitled "Methods and Devices to Control Fluid Volumes, Reagent and Particle Concentration in Arrays of Microfluidic Drops," which is hereby incorporated by reference in its entirety.

Figure 2:
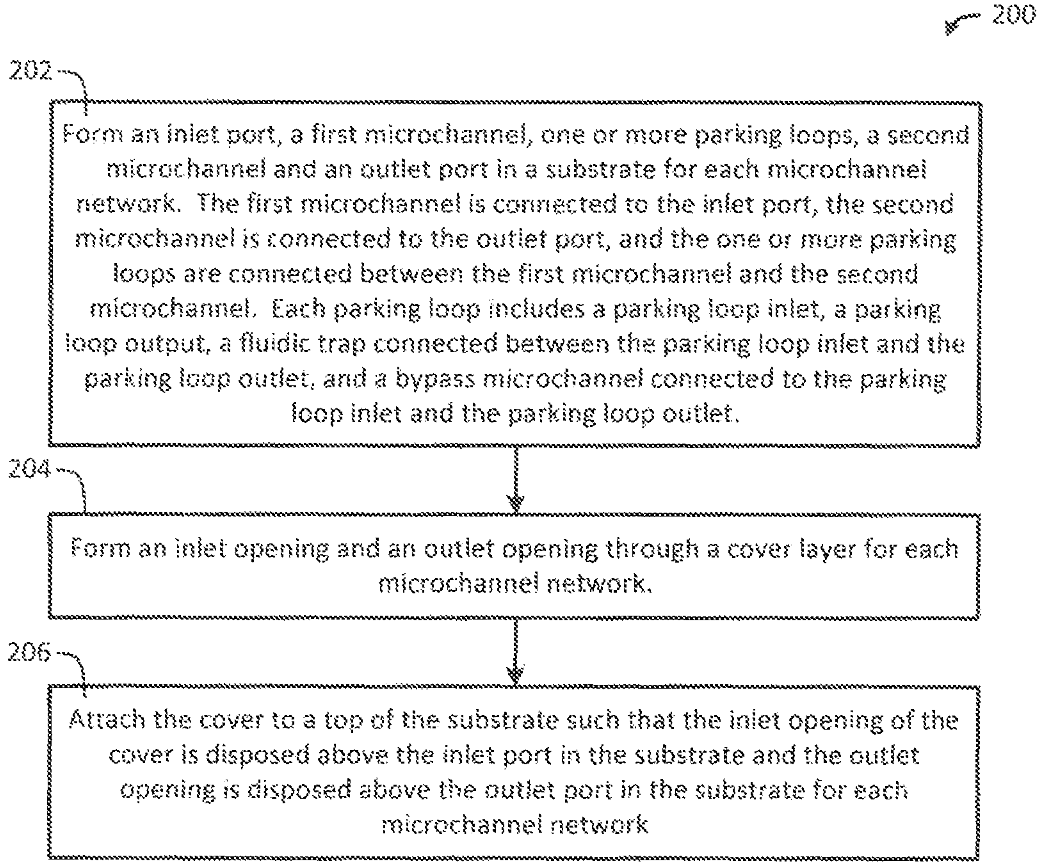
FIG. 2 is a flow chart of a method of making a microfluidic device in accordance with one embodiment of the present invention.

Now referring to FIG. 2, a flow chart of a method 200 of making a microfluidic device having one or more microchannel networks in accordance with one embodiment of the present invention is shown. An inlet port, a first microchannel, one or more parking loops, a second microchannel and an outlet port are formed in a substrate for each microchannel network in block 202. The first microchannel is connected to the inlet port, the second microchannel is connected to the outlet port, and the one or more parking loops are connected between the first microchannel and the second microchannel. Each parking loop includes a parking loop inlet, a parking loop output, a fluidic trap connected between the parking loop inlet and the parking loop outlet, and a bypass microchannel connected to the parking loop inlet and the parking loop outlet. An inlet opening and an outlet opening are formed through a cover layer for each microchannel network in block 204. The cover is attached to a top of the substrate in block 206 such that the inlet opening of the cover is disposed above the inlet port in the substrate and the outlet opening is disposed above the outlet port in the substrate for each microchannel network. Note that the forming steps can be repeated to form an array microchannel networks.

Figure 3:
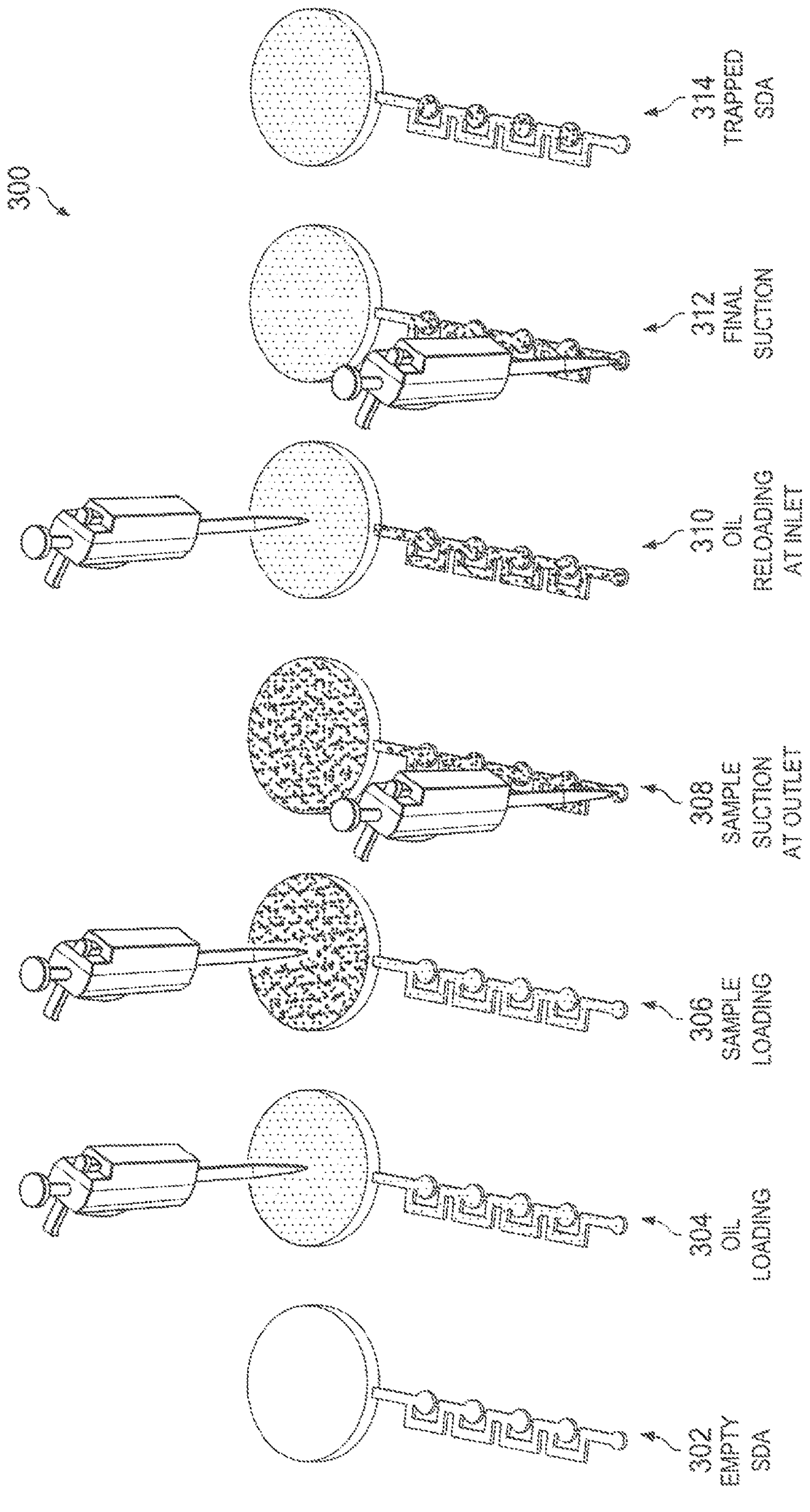
FIG. 3 illustrates a method using pipette-integrated trapping in a single microchannel network in accordance with one embodiment of the present invention.

Referring now to FIG. 3, a method 300 using pipette-integrated trapping in a single microchannel network in accordance with one embodiment of the present invention is shown. The method 300 involves 5 times pipetting (3 times dispensing, 2 times suctioning). An empty static droplet array (SDA) (e.g., microchannel network 104) is provided at step 302. In step 304, the channel is primed with oil by releasing 5 μL oil in the inlet port reservoir of the SDA using a pipette. The oil moves through the channel by a capillary suction. As soon as the oil is reached to the outlet, a 1.5 μL sample (dye in water or cells in media) is dispensed at the inlet-port using pipette in step 306. Then suction is created at the outlet port by pressing and releasing the dispense trigger of pipette with an empty tip in step 308. The suction creates a moving plug of the sample from the inlet port, which fills the channel and fluidic traps. Then 10 μL oil is reloaded at the inlet-port using pipette in step 310. Another suction is created at outlet port using empty pipette tip in step 312. This final suction removes the sample from the channel leaving the trapped samples inside the fluidic traps as shown in step 314. Note that the oil and sample volumes above will vary depending on the size and configuration of the SDA.

Figure 4:
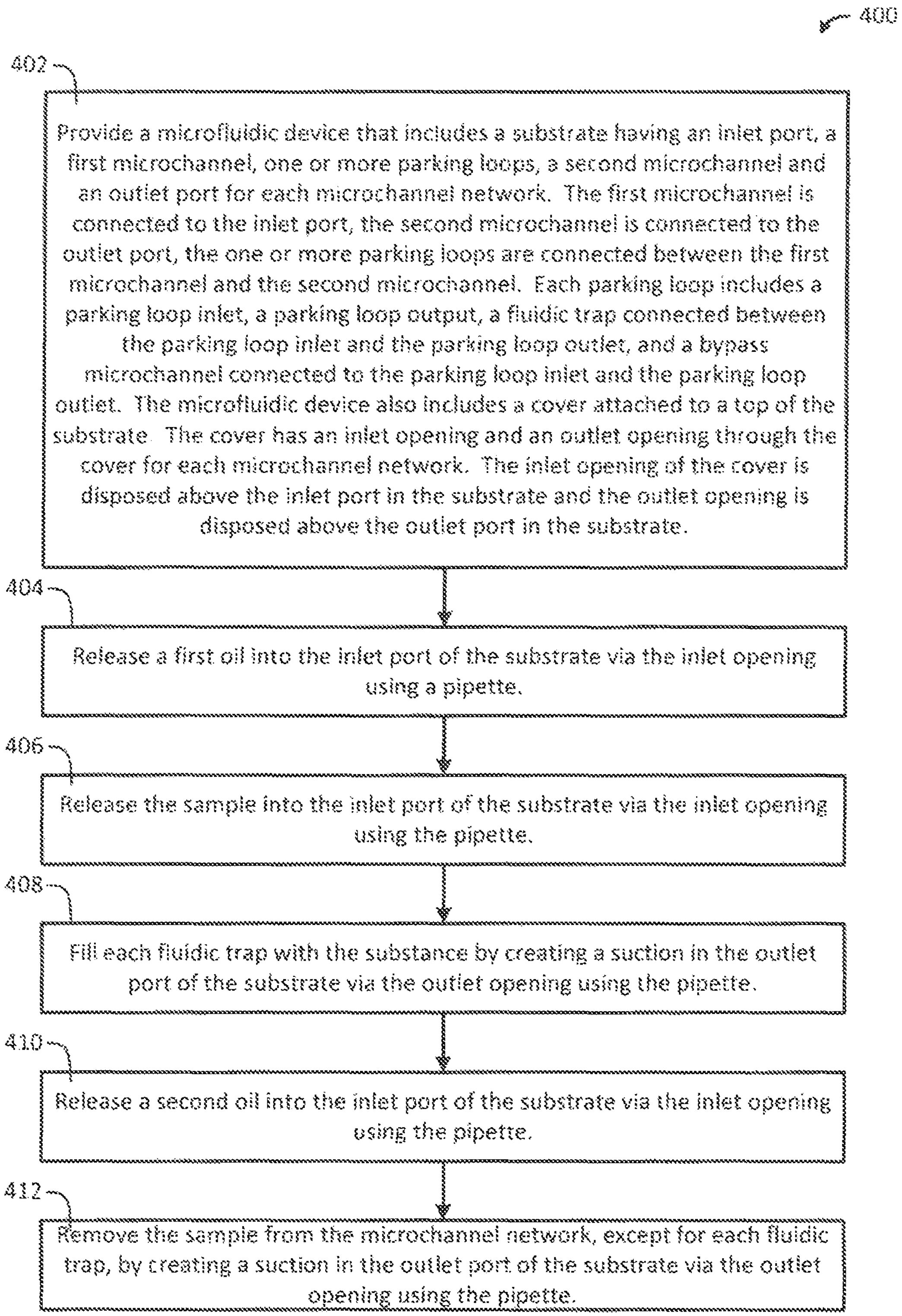
FIG. 4 is a flow chart of a method 400 for trapping a sample within a microfluidic device having one or more microchannel networks in accordance with one embodiment of the present invention.

Similarly, FIG. 4 is a flow chart of a method 400 for trapping a sample within a microfluidic device having one or more microchannel networks in accordance with one embodiment of the present invention. A microfluidic device is provided in block 402. The microfluidic device includes a substrate having an inlet port, a first microchannel, one or more parking loops, a second microchannel and an outlet port for each microchannel network. The first microchannel is connected to the inlet port, the second microchannel is connected to the outlet port, the one or more parking loops are connected between the first microchannel and the second microchannel. Each parking loop includes a parking loop inlet, a parking loop output, a fluidic trap connected between the parking loop inlet and the parking loop outlet, and a bypass microchannel connected to the parking loop inlet and the parking loop outlet. The microfluidic device also includes a cover attached to a top of the substrate. The cover has an inlet opening and an outlet opening through the cover for each microchannel network. The inlet opening of the cover is disposed above the inlet port in the substrate and the outlet opening is disposed above the outlet port in the substrate. A first oil is released into the inlet port of the substrate via the inlet opening using a pipette in block 404. The sample is released into the inlet port of the substrate via the inlet opening using the pipette in block 406. Each fluidic trap is filled with the substance by creating a suction in the outlet port of the substrate via the outlet opening using the pipette in block 408. A second oil is released into the inlet port of the substrate via the inlet opening using the pipette in block 410. The sample is removed from the microchannel network, except for each fluidic trap, by creating a suction in the outlet port of the substrate via the outlet opening using the pipette in block 412.

Note that the pipette can be automatically controlled with a processor communicably coupled to the pipette. Moreover, multiple microchannel networks can be filled simultaneously. For example, a first microchannel network can contain the sample having a first concentration, a second microchannel network can contains the sample having a second concentration. Likewise, a first microchannel network can contain a first sample, and a second microchannel network can contain a second sample. The sample may include one or more drops, cells or compositions.

Various embodiments of the present invention were tested as described below. Solutions of red, green, blue, purple and orange dyes (McCormick) were diluted 10× by distilled water and used as reagent plugs. 0.001% (w/w) biocompatible fluorosurfactant, KrytoxFSH-PEG600-KrytoxFSH (RAN Biotechnologies, Inc., MA) in FC-40 (Sigma-Aldrich) was used as carrier fluid. Human leukemia cancer cell line CCRF-CEM was maintained and grown in RPMI-1640 medium containing 10% fetal bovine serum and 0.1% Insulin-Transferrin-Selenium at 37° C. in 5% CO2. Cell density of 3.5×106 cells/mL was used in the experiments. LIVE/DEAD® Cell Imaging Kit (Life technologies) was used to stain the cells for the cell viability test. Preliminary cytotoxicity assays performed with the anticancer drug doxorubicin.

Figure 5B:
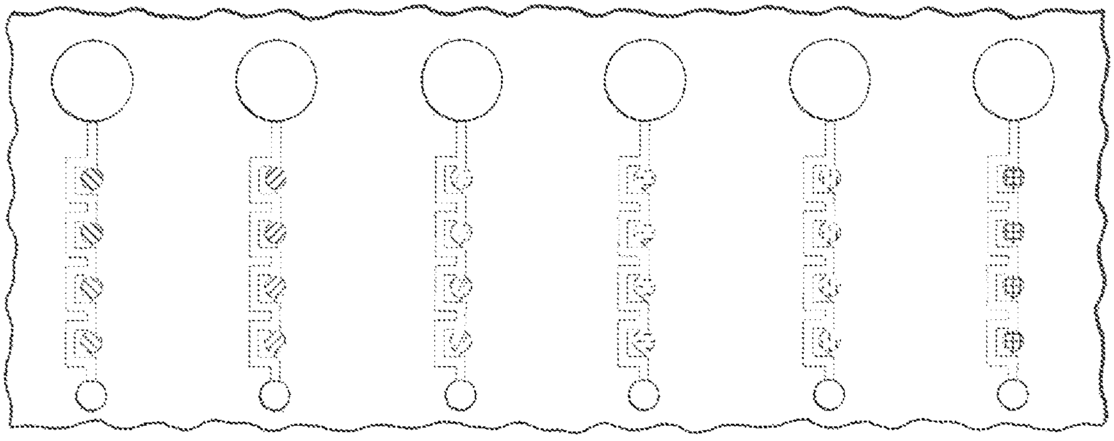
FIGS. 5A and 5B are images shows the versatility of a pipette-integrated microfluidic well plate device in accordance with the present invention in which different concentration of green dye in distilled water stored in a single microfluidic well plate device (FIG. 5A) and different dyes in distilled water stored in a single microfluidic well plate device of the SDA (FIG. 5B)
Figure 5A:
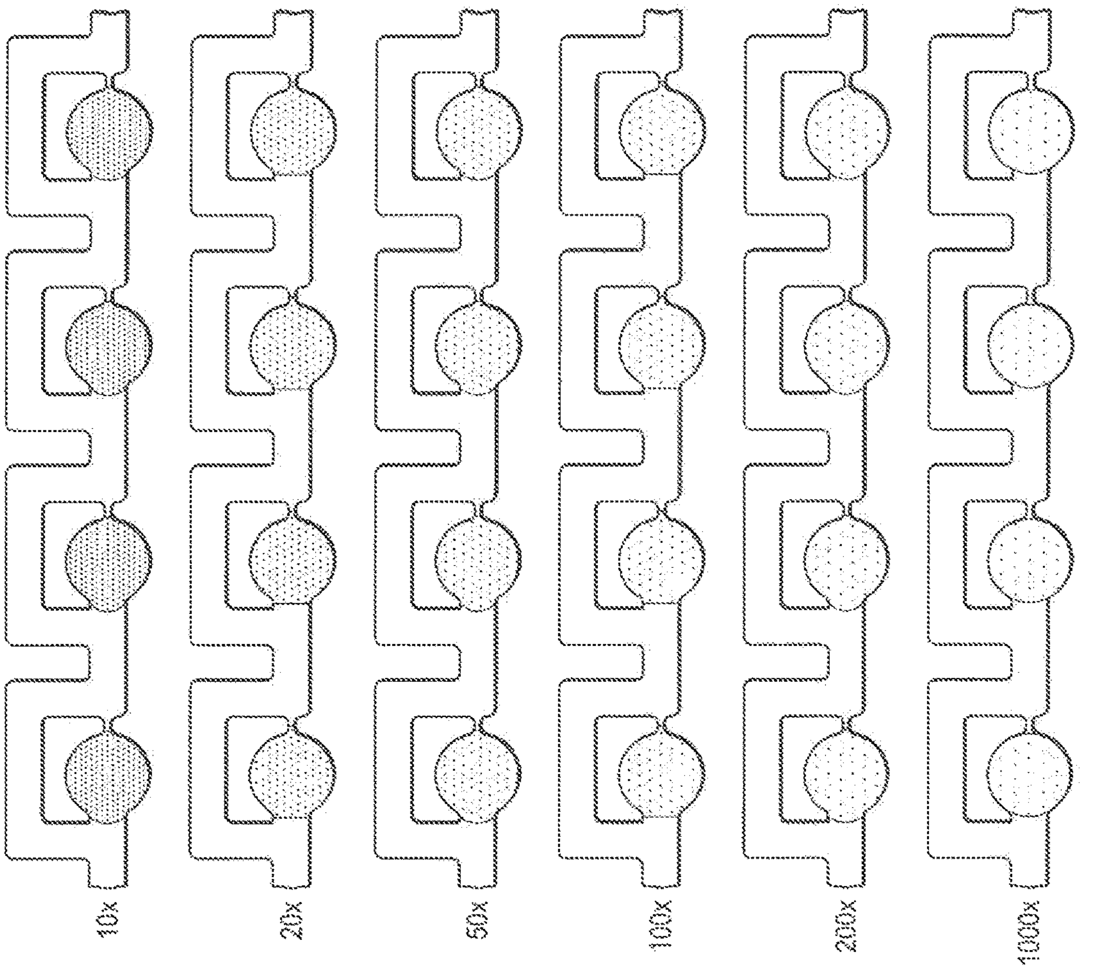

The versatility of the pipette-integrated microfluidic well plate device in accordance with the present invention is illustrated in FIGS. 5A and 5B. FIG. 5A shows different concentrations of green dye in distilled water (10×, 20×, 50×, 100×, 200× and 1000×) stored in a single microfluidic well plate device. FIG. 5B shows different dyes in distilled water stored in a single microfluidic well plate device of the SDA. The channel and the ports are filled with the residual oil. Different concentrations of the same sample can be trapped in different SDAs (FIG. 5A) on the single microfluidic well plate device. Likewise, different samples can be trapped in different SDAs (FIG. 5B) on a single microfluidic well plate device.

Figure 6:
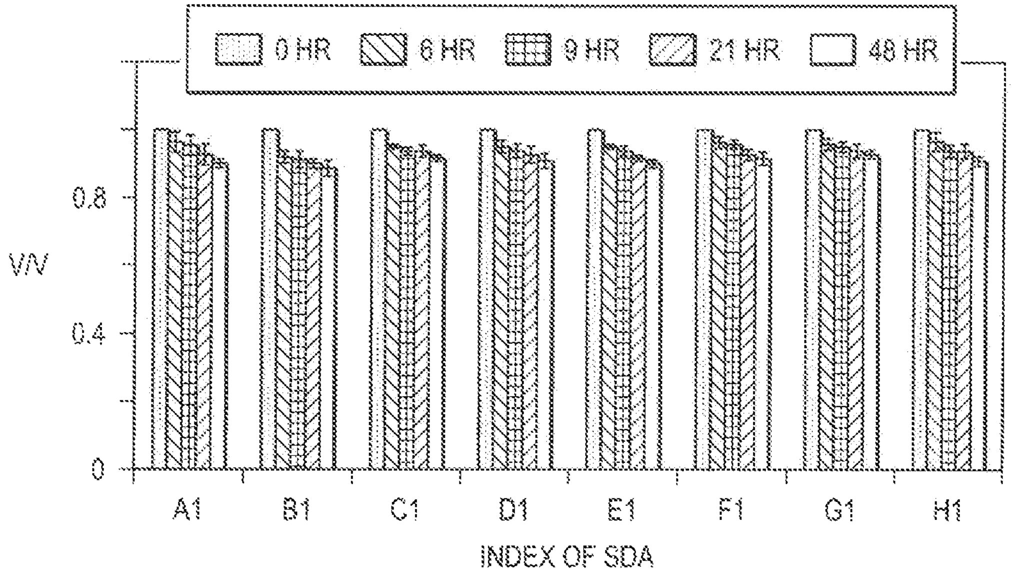
FIG. 6 is a graph showing the trapped drop volume conservation data over 2 days in 8-SDAs.

To perform cell culture or drug dose response assay in nanoliter-scale, the preservation of drop content over a period of time is very crucial. To avoid the liquid evaporation from the trapped drop over time, oil-filled pipette tips were initially used in both of the ports of the device. However, an ~30% sample evaporation was observed over 48 hours. Therefore, several strategies for reducing the evaporation during the incubation were explored. An effective method involves the plasma bonding of a second layer of PDMS sheet of 1 mm thickness with 3 mm holes aligned with the inlet and outlet ports of each SDA in the bottom layer. Then, the device is soaked in distilled water for 3 days. After 3 days, the device is used and after finishing the droplet trapping process, all of the 3 mm holes in the second layer are filled with oil to create oil reservoirs above the inlet and outlet of the SDAs. Then, the device was put in water filled omni-plate with a lid and stored in the incubator. Potential loss of reagent fluid due to evaporation in this process was less than 10% during 48 hours. The data is shown in FIG. 6.

Figure 7:
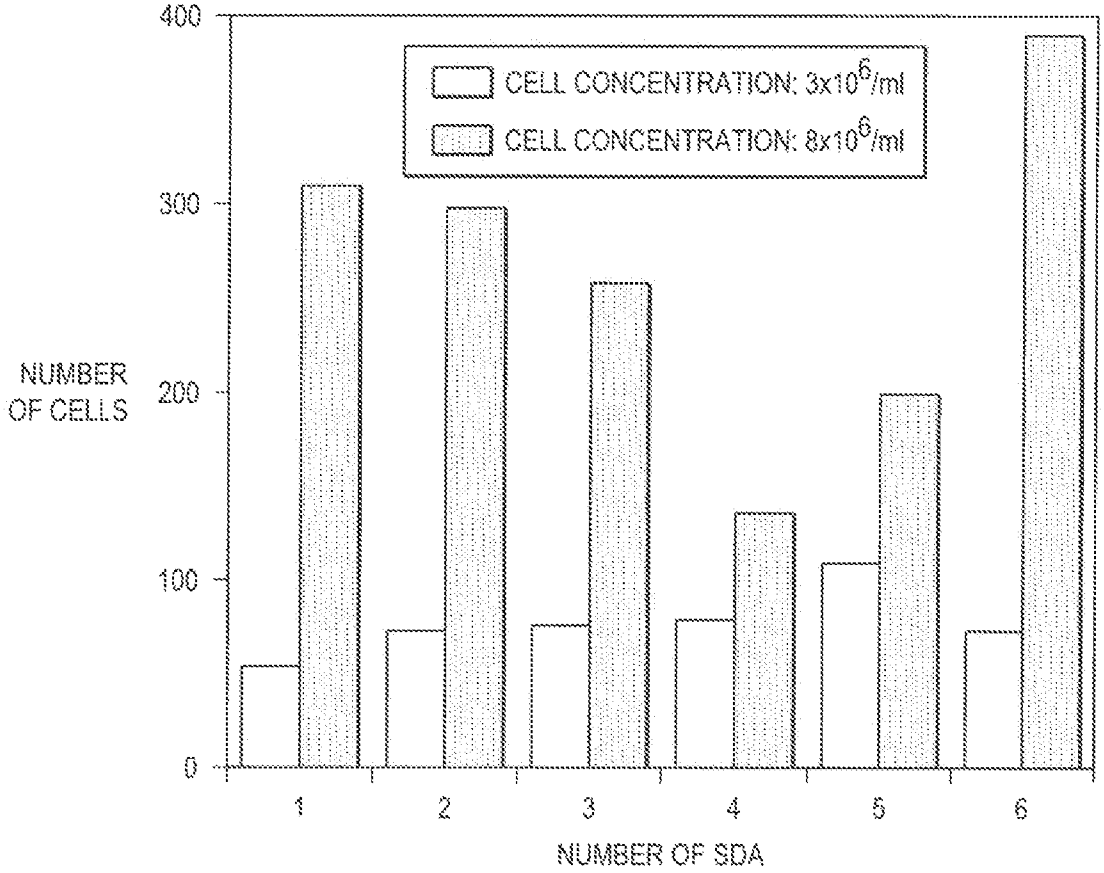
FIG. 7 is a graph showing the quantification of cell distribution for different stock cell concentrations.

The quantification of cell distribution in drops was also tested. Different stock cell densities were used to get an idea of cell distribution in each microchannel using pipette-integrated droplet trapping. Two stock solutions of cells (density of 3×106 and 8×106 cells/mL) with a target of 50-250 cells/drop were prepared to get about 200-1000 cells per SDA, which gave a better statistic for future assay analysis. The actual cell distribution in 6-SDAs is shown in FIG. 7, which is less than 50% of the expected number of cells/SDA.

Figure 8:
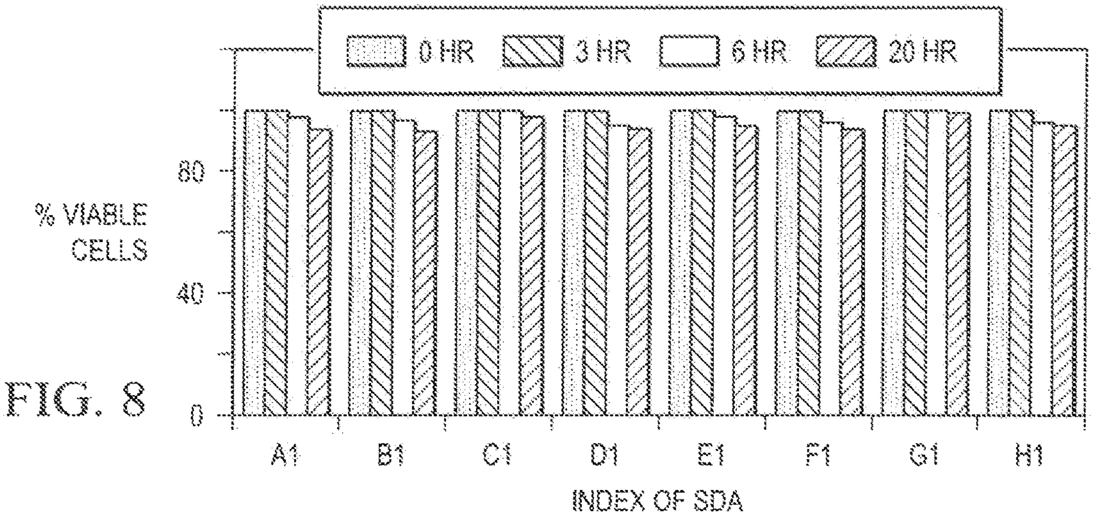
FIG. 8 is a graph showing the viability of controlled cell assay.

Previously, cell viability in 16 nL drop of a density of 30 cells/drop was tested. The previous data showed greater than 90% cells are viable up to 4.5 hours without any media replacement. A similar cell viability test was performed using the microfluidic device in accordance with the present invention with a 30 nL drop volume. A cell density of 3×106 cells/mL was used to get about 100 cells per SDA to assess the viability of cells during the culture. Cells diluted with only media and without any drugs are used as controls. The cells are staining with live and dead fluorescent dyes prior to the trapping process. Standard epifluorescence microscopy automated stage was used with to image viable cells. A greater than 90% cell viability over 20 hours in 8-SDAs without any media replacement was observed. The results are shown in FIG. 8.

Figure 9A:
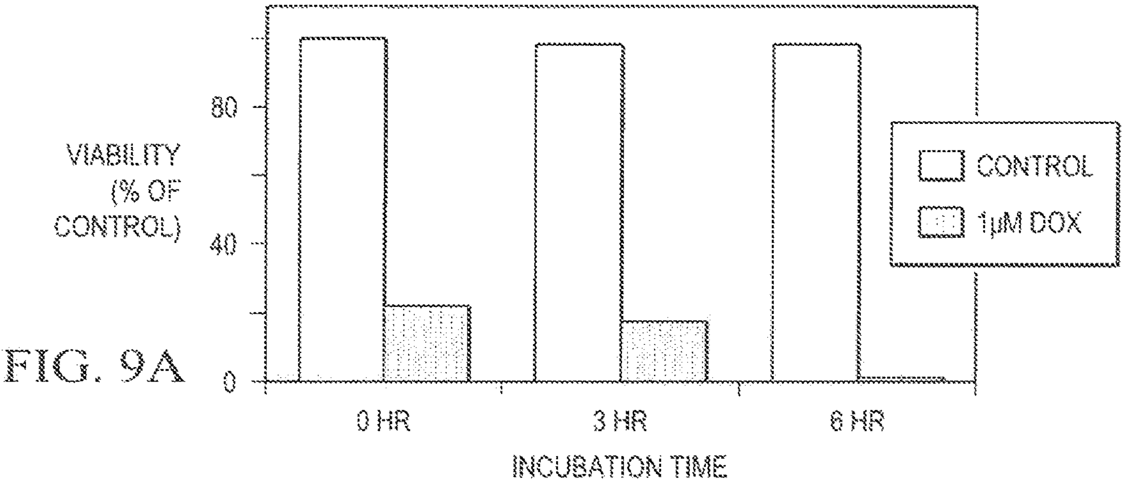
FIG. 9A is graph showing the effect of the anticancer drug doxorubicin on cell viability.

In addition, preliminary cytotoxicity assays were performed using the anticancer drug doxorubicin in the microfluidic device in accordance with the present invention. A concentration 0.75×106 cells/mL strained with live/dead cell imaging kit was used. In one SDA controlled cell trapping (without drug) was performed and in another SDA the cells were exposed to 1 μM doxorubicin before trapping and the cell viability over time was observed in both of the SDAs. Preliminary cytotoxicity assays with the anticancer drug doxorubicin showed greater than 99% cell death over 6 hour incubation period (FIG. 9A).

Figure 9B:
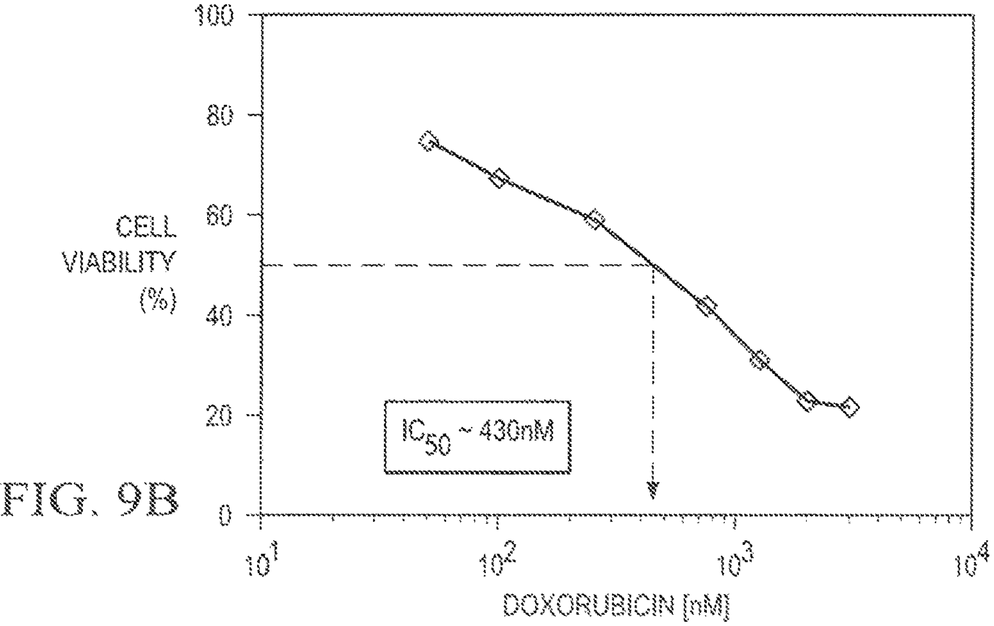
FIG. 9B is a graph showing the dose-dependent cytotoxicity of the doxorubicin for the leukemia cell line (CCRF-CEM)

Further, to determine dose-dependent cytotoxicity of the doxorubicin, leukemia cells were exposed to different concentrations of drug and each concentration treated cells were trapped in a separate SDA of the microfluidic device, and then the device was incubated for 1 hour, after which the cell viability was determined by standard image based epifluorescence microscopy. The IC50 value of the doxorubicin in the leukemia cell lines was found 430 nM (FIG. 9B).

The foregoing description of the apparatus and methods of the invention in preferred and alternative embodiments and variations, and the foregoing examples of processes for which the invention may be beneficially used, are intended to be illustrative and not for purpose of limitation. The invention is susceptible to still further variations and alternative embodiments within the full scope of the invention, recited in the following claims.

The invention claimed is:

1. A method for storing a sample within a microfluidic device having one or more microchannel networks comprising:

providing the microfluidic device comprising:

a substrate having an inlet port, a first microchannel, one or more parking loops, a second microchannel and an outlet port for each microchannel network, wherein the first microchannel is connected to the inlet port, the second microchannel is connected to the outlet port, the one or more parking loops are connected between the first microchannel and the second microchannel, and each parking loop comprises a parking loop inlet, a parking loop output, a fluidic trap connected between the parking loop inlet and the parking loop outlet, and a bypass microchannel connected to the parking loop inlet and the parking loop outlet, and a cover attached to a top of the substrate, the cover having an inlet opening and an outlet opening through the cover for each microchannel network, wherein the inlet opening of the cover is disposed above the inlet port in the substrate and the outlet opening is disposed above the outlet port in the substrate;

storing the sample within the microfluidic device by:

releasing a first oil into the inlet port of the substrate via the inlet opening using a pipette and allowing the first oil to move from the inlet port to the outlet port by a capillary suction;

releasing the sample into the inlet port of the substrate via the inlet opening using the pipette;

filling each fluidic trap with the sample by creating a suction in the outlet port of the substrate via the outlet opening using the pipette;

releasing a second oil into the inlet port of the substrate via the inlet opening using the pipette;

removing the sample from the first microchannel, the parking loop inlet, the bypass microchannel, the parking loop outlet and the second microchannel of each microchannel network using the second oil, and storing the sample in each fluidic trap, by creating a suction in the outlet port of the substrate via the outlet opening using the pipette; and filling the inlet port, the first microchannel, the second microchannel, the outlet port and the bypass channel of each parking loop with a third oil such that the sample remains in each fluidic trap and a level of the third oil is above the inlet port and the outlet port.

2. The method as recited in claim 1, wherein the fluidic trap comprises:

a trap repository connected to the parking loop inlet; and a trap microchannel connecting the trap repository to the parking loop outlet, wherein a cross-sectional area of the trap microchannel is smaller than a cross-sectional area of the bypass microchannel.

3. The method as recited in claim 2, wherein the trap repository has a volume of about 10, 20, 30, 40, 50, 60, 70, 80 or 90 nL.

4. The method as recited in claim 2, wherein:

the first microchannel, the second microchannel and the bypass microchannel have a width of about 200 μm and a height of about 200 μm;

the trap repository has a diameter of about 450 μm;

the trap microchannel has a width of about 40 μm; and the first microchannel, the second microchannel, the bypass microchannel, the trap repository and the trap microchannel have a height of about 200 μm.

5. The method as recited in claim 4, wherein the trap microchannel has a length of about 100 μm.

6. The method as recited in claim 1, further comprising the step of automatically controlling the pipette with a processor communicably coupled to the pipette.

7. The method as recited claim 6, wherein:

the one or more microchannel networks comprise two or more microchannel networks forming an array microchannel networks;

the pipette comprises one pipette for each microchannel network; and the method is performed simultaneously for the microchannel networks.

8. The method as recited claim 1, wherein:

the one or more microchannel networks comprise at least a first microchannel network and a second microchannel network;

the first microchannel network contains the sample having a first concentration; and the second microchannel network contains the sample having a second concentration.

9. The method as recited claim 1, wherein:

the one or more microchannel networks comprise at least a first microchannel network and a second microchannel network;

the sample comprises a first sample and a second sample;

the first microchannel network contains the first sample; and the second microchannel network contains the second sample.

10. The method as recited in claim 1, wherein the sample comprises one or more drops, cells or compositions.

11. The method as recited in claim 1, wherein a hydrodynamic resistance ratio between the fluidic trap and the bypass microchannel is from 1.0 to 2.0, and a hydrodynamic resistance of the bypass microchannel is smaller than a hydrodynamic resistance of the fluidic trap.

12. The method as recited in claim 1, wherein a hydrodynamic resistance ratio between the fluidic trap and the bypass microchannel is from 1.4 to 1.6, and a hydrodynamic resistance of the bypass microchannel is smaller than a hydrodynamic resistance of the fluidic trap.

13. The method as recited in claim 1, wherein the one or more parking loops comprise at least four parking loops.

14. The method as recited in claim 1, wherein the one or more microchannel networks comprise two or more microchannel networks forming an array microchannel networks.

15. The method as recited in claim 1, wherein a diameter of the inlet opening and the outlet opening of the cover have a diameter of about 3 mm.

16. The method as recited in claim 1, wherein:

the inlet port in the substrate comprises a reservoir; and the inlet opening of the cover is aligned with the reservoir in the substrate.

17. The method as recited in claim 1, wherein the cover reduces an evaporation of the sample stored in the fluidic trap(s) and increases a viability of the sample stored in the fluidic trap(s).

18. The method as recited in claim 17, wherein the evaporation of the sample stored in the fluidic trap(s) is less than 10% during 48 hours.

19. The method as recited in claim 1, further comprising soaking the microfluidic device in a distilled water prior to storing the sample within the microfluidic device.

20. The method as recited in claim 1, further comprising placing the microfluidic device in a water filled omni-plate with a lid after storing the sample within the microfluidic device.

* * * * *